United States Patent
Knickerbocker et al.

(10) Patent No.: US 10,258,142 B2
(45) Date of Patent: Apr. 16, 2019

(54) TOOTHBRUSH WITH SENSORS

(71) Applicant: International Business Machines Corporation, Armonk, NY (US)

(72) Inventors: John U. Knickerbocker, Monroe, NY (US); Minhua Lu, Mohegan Lake, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 586 days.

(21) Appl. No.: 14/942,522

(22) Filed: Nov. 16, 2015

(65) Prior Publication Data

US 2017/0135464 A1    May 18, 2017

(51) Int. Cl.
| | |
|---|---|
| *A61B 5/00* | (2006.01) |
| *A46B 15/00* | (2006.01) |
| *A46B 17/08* | (2006.01) |
| *A46B 9/04* | (2006.01) |
| *A46B 11/00* | (2006.01) |
| *G09G 5/00* | (2006.01) |

(52) U.S. Cl.
CPC ............ *A46B 15/0004* (2013.01); *A46B 9/04* (2013.01); *A46B 11/002* (2013.01); *A46B 15/0044* (2013.01); *A46B 17/08* (2013.01); *A61B 5/00* (2013.01); *A46B 2200/1066* (2013.01); *G09G 5/00* (2013.01)

(58) Field of Classification Search
CPC . A61C 17/227; A61C 17/0202; A61C 17/221; A61C 17/028; A61C 1/0015; A61C 17/0217; A61C 1/0084; A61C 1/0092; A46B 9/04; A46B 15/0004; A46B 13/04; A46B 15/0022; A61B 10/0051; A61B 5/4547

USPC ......................................... 600/573, 575, 578
See application file for complete search history.

(56) References Cited

U.S. PATENT DOCUMENTS

| 5,909,977 A * | 6/1999 | Kuo ..................... A46B 11/002 401/146 |
| 6,102,872 A * | 8/2000 | Doneen ............... A61B 5/14532 422/50 |

(Continued)

FOREIGN PATENT DOCUMENTS

CN         202458291 U    10/2012

OTHER PUBLICATIONS

Zafar et al., "A comparison between bipolar transistor and nanowire field effect transistor biosensors," Applied Physics Letters 106, 063701 (Feb. 2015).

(Continued)

*Primary Examiner* — May A Abouelela
(74) *Attorney, Agent, or Firm* — Vazken Alexanian; Michael J. Chang, LLC

(57) ABSTRACT

Smart toothbrush designs are provided. In one aspect, a toothbrush is provided which includes: a handle portion; and a head portion attached to the handle portion, wherein the head portion has bristles, a sample testing chamber containing at least one electronic sensor, a removable tip for drawing saliva samples into the sample testing chamber, and a calibration solution reservoir connected to the sample testing chamber. In another aspect, the head portion of the toothbrush has at least one optical sensor. A method for acquiring user data using the present smart toothbrush designs is also provided.

16 Claims, 5 Drawing Sheets

(56) References Cited

U.S. PATENT DOCUMENTS

| | | | |
|---|---|---|---|
| 6,106,294 A * | 8/2000 | Daniel | A46B 15/0002 15/105 |
| 6,623,698 B2 | 9/2003 | Kuo | |
| 6,960,170 B2 | 11/2005 | Kuo | |
| 7,314,453 B2 * | 1/2008 | Kuo | A61B 5/14532 600/309 |
| 8,803,095 B2 * | 8/2014 | Gronlund | A46B 15/0002 250/339.07 |
| 8,920,746 B2 | 12/2014 | Hohlbein et al. | |
| 8,938,838 B2 | 1/2015 | Vashi | |
| 9,282,811 B2 * | 3/2016 | Grez | A46B 15/001 |
| 9,901,430 B2 * | 2/2018 | Boughorbel | A61C 17/221 |
| 2002/0127143 A1 * | 9/2002 | Kuo | A61B 10/0051 422/68.1 |
| 2005/0272002 A1 * | 12/2005 | Chenvainu | A61C 1/0061 433/80 |
| 2007/0270221 A1 | 11/2007 | Park et al. | |
| 2009/0317770 A1 | 12/2009 | Gatzemeyer et al. | |
| 2012/0003601 A1 | 1/2012 | Hunter et al. | |
| 2012/0021375 A1 * | 1/2012 | Binner | A61B 5/097 433/89 |
| 2014/0272768 A1 * | 9/2014 | Curry | A61B 5/0088 433/27 |
| 2016/0338635 A1 * | 11/2016 | Johnson | A61B 5/4547 |
| 2017/0007215 A1 * | 1/2017 | Podoly | A61C 17/046 |
| 2017/0324277 A1 * | 11/2017 | Mitcheson | H02J 50/12 |

OTHER PUBLICATIONS

Trnkova et al., "Amphoteric Sensor for Detection of Chloride Ions," Sensors, 8, 5619-5636 (Sep. 2008).

Das et al., "Mechanistic Influence of Nanometer Length-Scale Surface Chemistry on DNA Hybridization," ACS Nano, 9 (7), pp. 7466-7478 (Jun. 2015).

Karen Jonusz et al., "Impact of a Novel Power Toothbrush with SmartGuide Technology on Brushing Pressure and Thoroughness," Journal of Contemporary Dental Practice, vol. 9, No. 7, pp. 1-13 (Nov. 1, 2008).

Aditi Pai, "Kolibree crowdfunds its smartphone-enabled electric toothbrush on Kickstarter," Apr. 2014 (2 pages).

English Abstract of CN202458291U by Jian Huang, Oct. 3, 2012.

* cited by examiner

TOOTHBRUSH WITH SENSORS

FIELD OF THE INVENTION

The present invention relates to smart toothbrush designs, and more particularly, to smart toothbrushes with sensors configured to collect and analyze user data, and provide feedback.

BACKGROUND OF THE INVENTION

Much health-related information can be garnered from the conditions in a subject's mouth. For instance, oral hygiene and/or other health based diagnostics can be made based on samples taken from a person's mouth. See, for example, U.S. Patent Application Publication Number 2009/0317770 by Gatzemeyer et al., entitled "User Health Profiles Derived from Oral Care Implements" (hereinafter "U.S. Patent Application Publication Number 2009/0317770"). For instance, in U.S. Patent Application Publication Number 2009/0317770, user health profiles are created based on readings taken while a person is brushing their teeth. Incorporating such diagnostics with toothbrushing activities is convenient since people routinely brush their teeth at least once a day, and thus do not have to undertake a separate routine for performing these other tests.

Improved techniques for effectively and reliably collecting and testing samples are however needed for such technology to be implemented for widespread and accurate health based diagnostics.

SUMMARY OF THE INVENTION

The present invention provides smart toothbrush designs with sensors configured to collect and analyze user data, and provide feedback. In one aspect of the invention, a toothbrush is provided. The toothbrush includes: a handle portion; and a head portion attached to the handle portion, wherein the head portion comprises bristles, a sample testing chamber containing at least one electronic sensor, a removable tip for drawing saliva samples into the sample testing chamber, and a calibration solution reservoir connected to the sample testing chamber.

In another aspect of the invention, another toothbrush is provided. The toothbrush includes: a handle portion; and a head portion attached to the handle portion, wherein the head portion comprises bristles, and at least one optical sensor.

In yet another aspect of the invention, a method for acquiring user data is provided. The method includes the steps of: collecting data from a user during toothbrushing using a toothbrush having a handle portion and a head portion attached to the handle portion, wherein the head portion includes bristles, a sample testing chamber containing at least one electronic sensor, a removable tip for drawing saliva samples into the sample testing chamber, and a calibration solution reservoir connected to the sample testing chamber; analyzing the data; and providing feedback based on the analyzed data. The head portion of the toothbrush may further include at least one optical sensor.

A more complete understanding of the present invention, as well as further features and advantages of the present invention, will be obtained by reference to the following detailed description and drawings.

DETAILED DESCRIPTION OF PREFERRED EMBODIMENTS

Figure 1:
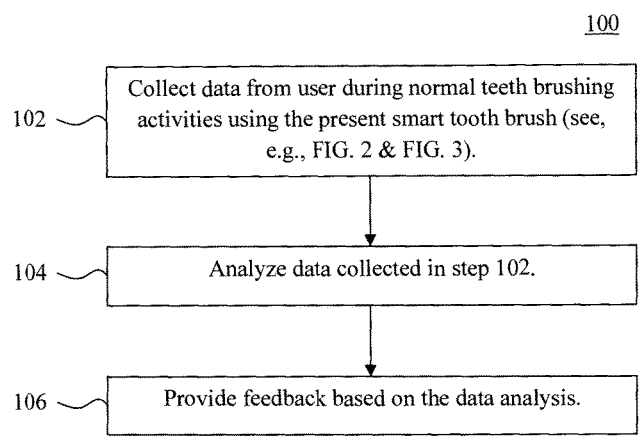
FIG. 1 is a diagram illustrating an exemplary methodology for acquiring user data during brushing using a smart toothbrush according to an embodiment of the present invention.

The present techniques provide what is termed herein as a "smart" toothbrush design whereby sensors within the toothbrush collect health information about the user. The smart toothbrush design is integrated with conventional toothbrush functionalities, such that the user health data can be easily and effectively collected during the performance of routine tooth cleaning operations by the user. For instance, the present smart toothbrush design includes a handle and a head, the head containing bristles and/or other tooth-cleaning structures commonly passed over the tooth surface, gums, etc. to clean one's teeth. The data collected from the user is then processed, and information is provided to the user and/or to other parties (such as health care professionals) about the user's health. For instance, the present smart toothbrush may contain a screen (for example embedded in the toothbrush handle) that displays useful information to the user, such as information relating to the user's oral hygiene, i.e., presence of plaque, bacteria, etc. so that the user can alter their brushing procedure and/or seek input from a medical professional. Such information can also be sent in a similar manner to a user's smart phone.

The term "user" refers generally herein to any individual for which the present smart toothbrush is used to clean their teeth. For instance, health data can be easily and effectively collected for human users of the present system. However, many pet owners also routinely clean their pet's teeth in the same general manner. Thus, information may also be collected for non-human users, such as dogs and cats.

As will be described in detail below, the present smart toothbrush platform includes the following components. Sensors—as will be provided in the exemplary embodiments described below, the present smart toothbrush design can include electronic (e.g., bipolar junction transistor (BTJ)-based) sensors and/or optical sensors. Embodiments are anticipated herein where electronic and optical sensors are employed in the same smart toothbrush to enhance the spectrum of data collected. Circuitry—as will be described in detail below, specific circuitry is needed for pump automation (e.g., during sample collection, reading, purging, etc.), sensing, amplification, data collection, data storage, power management, data transmission, etc. Power source— for practicality, the present smart toothbrush platform can be battery and/or super capacitor powered. The battery can be rechargeable using, for example, from a household power source, wireless charging, etc. Connectivity—as highlighted above, the information collected by the smart toothbrush platform can be transmitted to a user's smart phone or other receiver. This can be accomplished using a low power Bluetooth® or near field communications to transmit data to/from the smart tooth brush to the receiver and/or user's smart phone device. This technology can also provide a means to recharge the smart tooth brush device (i.e., via wireless charging) and/or store data until the time of transmission to the smart phone (e.g., while the device is in use or in storage). Security—since private (e.g., health-related) information is involved, encryption and personal identification tags and/or codes are preferably used to ensure the privacy of the user and/or to distinguish between multiple users in the same location. Environmentally friendly— environmentally friendly and bio-compatible electronics, sensors, power supply such as batteries, capacitors or other power source can be implemented in the present smart toothbrush design such that the device can be used and disposed after one or more uses without detrimental impact to the user or the environment.

An overview of the present techniques is now provided by way of reference to methodology 100 of FIG. 1. In step 102, real-time data is collected from a user during normal brushing activity. As highlighted above, normal brushing activities (which are generally performed on a regular basis—e.g., daily) involve brushing the bristles (or other similar cleaning structures) of the toothbrush over the teeth, gums, etc. to remove plaque, bacteria, food particles, etc. from the user's mouth. Here, in addition to the traditional functions of tooth brushing, health-related data is also collected. A vast amount of useful data can be collected from a user's mouth. For instance, the user's oral health can be analyzed based on plaque, bacteria, etc. detection. Further, more widespread health metrics can also be employed based on samples collected from a user's mouth during teeth brushing. For instance, saliva samples can be tested for the presence of chemicals, protein and bio markers that are indicators of disease, hormonal, anxiety, stress, etc. Exemplary smart toothbrush designs for collecting the data are provided below. For instance, in one exemplary embodiment, the smart brush platform includes a means for drawing a defined amount of saliva from the user (during brushing) and analyze the saliva sample via one or more calibrated, electronic sensors (e.g., solid state BTJ-based sensors). In another exemplary embodiment, the smart toothbrush platform includes optical sensors and imaging capabilities. For instance, a light source (e.g., a light-emitting diode or LED) and optical detector (e.g., a camera or spectrometer) is incorporated into the head of the smart toothbrush. A dyed mouth rinse or toothpaste can be used prior to/during brushing to mark bacteria. The dye can be detected via the optical sensors and can indicate where in the mouth the user might need to spend more time brushing.

The data collected in step 102 is then analyzed in step 104. Data analysis can be performed on the smart toothbrush platform itself and/or via a remote computer. For instance, the smart toothbrush may have micro-processing and data storage capabilities that can be used to analyze, encrypt/ protect, and store the data directly on the platform itself. As provided above, data protection, such as encryption or coding, is important to maintain the confidentiality of an individual's health data (e.g., such as in settings where the smart toothbrush is accessible/used by multiple individuals). The data can also be transmitted (e.g., wirelessly, through data syncing, etc.) from the smart toothbrush platform to another device for processing. For instance, data collected by the smart toothbrush platform can be transmitted (e.g., via Bluetooth®) to the user's smart phone where it is analyzed.

In step 106, feedback from the analyzed data is presented to the user and/or to other parties (such as health care professionals). For instance, according to an exemplary embodiment, the present smart toothbrush platform includes a display (for instance on its handle) that provides information to the user. That information can include feedback on the data analyzed above. For instance, the information might provide the user with a profile of data gleaned from the saliva sample, and some analyses of potential impacts, such as bio markers for disease, stress detection, etc. The display is not limited to providing only text-based feedback to the user, and other visual indicators are anticipated herein. For example, the display may flash and/or display different colors to get the attention of the user. For instance, if the data indicates that there is tartar or bacteria buildup somewhere in the user's mouth, the display might change colors (e.g., display a red screen) and/or flash to indicate that the user should continue brushing in a certain area (i.e., until an indication is given to stop).

Health care professionals might also be enlisted to monitor the user's health conditions via the data collected using the smart toothbrush platform. For instance, a multi-daily brushing routine will provide a large amount of data that can be compiled and analyzed to create a health profile for the user over a certain period of time. For instance, the data sent to health care professionals via the present smart toothbrush platform can provide a real-time snapshot of various chemicals, proteins, bio markers, etc. that can be used to assess disease and other health related risks, etc.

Figure 2:
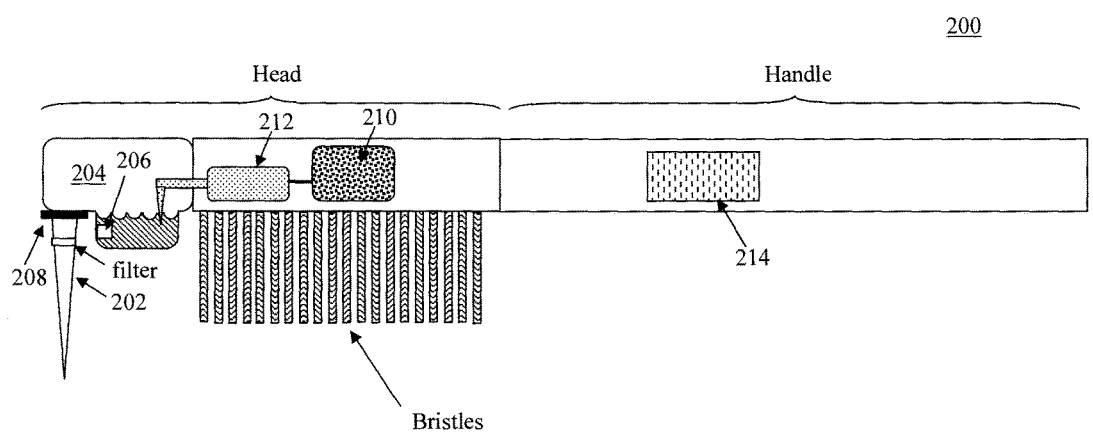
FIG. 2 is a diagram illustrating an exemplary smart toothbrush design having electronic sensors according to an embodiment of the present invention.
Figure 3:
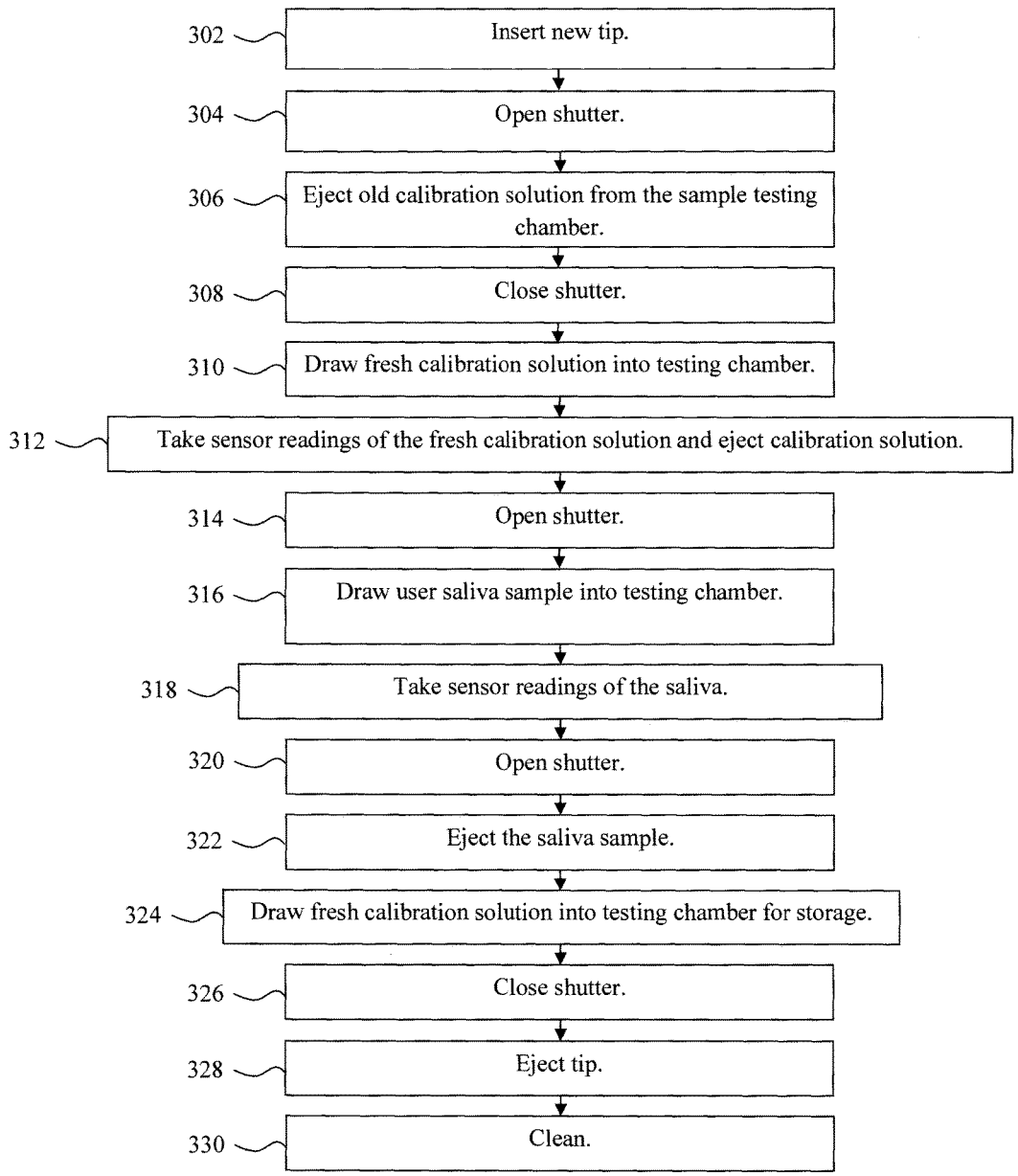
FIG. 3 is a diagram illustrating an exemplary methodology for acquiring user data via the smart toothbrush design of FIG. 2 according to an embodiment of the present invention.

An exemplary configuration of the present smart toothbrush platform and use thereof to perform the steps of methodology 100 is now described by way of reference to FIGS. 2 and 3. In this example, a pump is used to draw a saliva sample from the user via a disposable tip located on the smart toothbrush, head. Electronic sensors (e.g., solid state BTJ-based sensors) are then used to analyze the sample.

Specifically, referring first to FIG. 2, the present smart toothbrush platform 200 has a head portion and a handle portion. In addition to the advances presented herein, the head portion also performs the brushing tasks commonly associated with a toothbrush. For instance, as shown in FIG. 2, the head portion of the toothbrush contains a plurality of bristles (and/or other structures) configured to remove plaque, bacteria, particulates, etc.) from a user's teeth. The handle portion is gripped by the user and used to position and move the head portion/bristles over the teeth.

In the exemplary embodiment shown in FIG. 2, in addition to the bristles, the head portion of the smart toothbrush includes a removable tip 202 for saliva sample collection, a sample testing chamber 204 (housing one or more electronic sensors 206), a shutter 208 for regulating fluid flow into/out of the testing chamber 204 (via the tip 202), a calibration solution reservoir 210, and a pump system 212 for drawing the saliva sample and calibration solution.

According to an exemplary embodiment, the tip 202 is fitted with a filter to remove food and other particulates from the saliva sample. By way of example only, the tip is a disposable plastic tip such as commercially available sterile, disposable pipette tips. As is known in the art, such tips fit snugly onto the end of a fluid port and, once the fluid is drawn, can be removed by hand and disposed, or ejected using other means (not shown) such as an ejector lever, etc.

The shutter 208 can be controlled by the pump system 212 such that the shutter is opened during saliva sample collection and then closed to prevent the sample and/or calibration solution from flowing back out through the tip. After testing, the shutter can again be opened to purge these fluids back through the tip.

The pump system 212 is configured to draw metered amounts of the saliva sample and the calibration solution via the tip 202 and calibration solution reservoir 210, respectively. Any variety of commercially-available vacuum pumps may be employed in the present platform as pump system 212. By way of example only, vacuum pumps are commonly used in pipette technology to draw and dispense precise, user-selected volumes of a liquid sample. This same technology can be employed herein. Further, if so desired, multiple pumps may be used, for instance, one to draw/dispense the saliva sample and one to draw/dispense the calibration solution. Although, both functions can be accomplished using the same pump.

The composition of the calibration solution in reservoir 210 is well defined. Further, the amount of the solution used during calibration is well defined. By way of example only, the calibration solution can be sodium chloride (NaCl) of a known/controlled pH. By way of example only, the calibration solution can be of known amount of NaCl at a controlled pH (i.e., a pH buffer solution with a known amount of NaCl. It is notable that, when not in use, the testing chamber 204 is filled with the calibration solution. This is done to minimize signal drifts and minimize errors in the reference electrode.

According to an exemplary embodiment, the electronic sensors 206 are solid state BTJ-based sensors. BTJ sensors for bio-assays are described, for example, in Zafar et al., "A comparison between bipolar transistor and nanowire field effect transistor biosensors," Applied Physics Letters 106, 063701 (February 2015) (hereinafter "Zafar"), the contents of which are incorporated by reference as if fully set forth herein. See, for example, the BTJ-based biosensor shown in FIG. 1 of Zafar. As described in Zafar, the biosensor has two components, a device and an extended base. The device is a heterojunction bipolar transistor or HBT which includes a heavily doped n-type polysilicon emitter, p-type doped silicon germanium (SiGe) base, and n-type doped silicon (Si) collector. The extended base includes a conducting sensing surface that is connected to the SiGe base at one end and the other end is immersed in the solution (in this case, in the calibration solution). The extended base also includes a reference electrode (e.g., an AgCl/Ag reference electrode). The sensing surface of the HBT is a titanium nitride (TiN) film having a pH sensitive surface potential. During a sensing operation, the collector current is the sensing current. The content of the solution (which is present between the sensing surface and the reference electrode) varies depending on the contents of the saliva sample. The content of the solution affects properties such as the surface potential of the sensing surface, and thereby affects the collector current.

As shown in FIG. 2, the smart toothbrush handle can include a readout display 214. As provided above, feedback can be provided to the user through such a display. For instance, data/data analyses, alerts, instructions, etc. may be displayed to the user. In addition to the readout display, the battery (and/or other power source) and peripheral electronics can also be housed in the handle.

FIG. 3 is a diagram illustrating an exemplary methodology 300 for using smart toothbrush 200 to collect data from a user during brushing. For instance, methodology 300 represents an exemplary process for operating smart toothbrush 200 when performing, for example, step 102 of FIG. 1. As provided above, when not in use, the testing chamber 204 is filled with the calibration solution to minimize signal drifts and minimize errors in the reference electrode. Therefore, just prior to use, in step 302 a new tip 202 is inserted, and in step 304 the shutter 208 is opened to permit the old calibration solution to be ejected from the sample testing chamber 204 in step 306. As provided above, the pump system 212 can be used to draw fluids into and eject fluids out of the sample testing chamber 204. The shutter is then closed in step 308.

In step 310, fresh calibration solution of a defined amount is drawn into the sample testing chamber 204 from the calibration solution reservoir 210 via the pump system 212. In step 312, (calibration) readings of the sensors 206 are taken based on the fresh solution, the readings are stored, and the calibration solution is ejected.

In step 314, the shutter 208 is again opened and, in step 316 a defined amount (~50 microliters ($\mu$L) of a saliva sample is drawn from the user's mouth (through the tip 202) into the sample testing chamber 204. As noted above, this sample is drawn via the pump system 212. In step 318, readings of the sensors 206 are taken based on saliva sample.

Once the readings have been made, the saliva sample is purged from the sample testing chamber 204. For instance, in step 320 the shutter 208 is opened and in step 322 the saliva sample is ejected out through the tip 202 (via action of the pump system 212). For storage, in step 324 the sample testing chamber 204 is filled with fresh calibration solution from the calibration solution reservoir 210 (via action of the pump system 212). The calibration solution that is drawn into the testing chamber in step 324 is, as described above, purged just prior to use, and is what is referred to in step 306 as the "old calibration solution."

In step 326, the shutter 208 is closed, and in step 328 the tip 202 is ejected. The data collected via this process can be analyzed in the manner described above. In this case, there is both calibration data (obtained prior to sample collection) and sample testing data which can be compared to test a variety of different parameters.

In step 330, post-use cleaning of the smart tooth brush may then be performed. According to an exemplary embodiment, step 330 involves cleaning/sterilization such as with a mouthwash antiseptic solution, anti-bacterial cleaning solution, steam, ultraviolet (UV) light, or combinations thereof. The cleaning/sterilization can be done between uses. Power, if any, needed during the sterilization procedures can be obtained from the device's battery, and/or household power used for recharging the battery, etc.

When not in use, the present smart toothbrush can be placed in a holder station which couples the toothbrush with means for recharging, exchanging data, cleaning, etc. See above. According to an exemplary embodiment, the holder station further includes means for calibrating the smart toothbrush for electrical and/or optical needs of the user. For instance, the holder station can contain fluids of known concentrations of desired measurement or reference materials and therefore provide calibration to one or more sensors in the electronic toothbrush. The platform station can have standardized reference materials or positions for calibration and therefore a user can have a personalized or prioritized set of sensor metrics they and/or their doctor would like to have monitored, and the appropriate calibration or reference materials can be utilized with this system. In addition a time stamp or history of data collected from the sensors could be managed in a smart phone or in the holder station and trends displayed or alarm set on any predefined limits for any of the targeted sensor data or call out for a repeat measurement for verification if sensor data is not as expected. An exemplary configuration of the holder station is provided in FIG. 7, described below.

Figure 4:
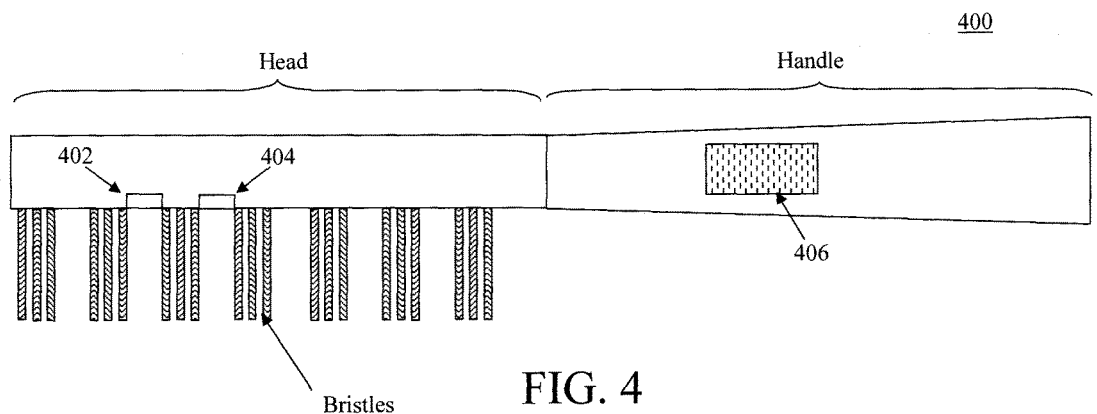
FIG. 4 is a diagram illustrating an exemplary smart toothbrush design having optical sensors according to an embodiment of the present invention.
Figure 5:
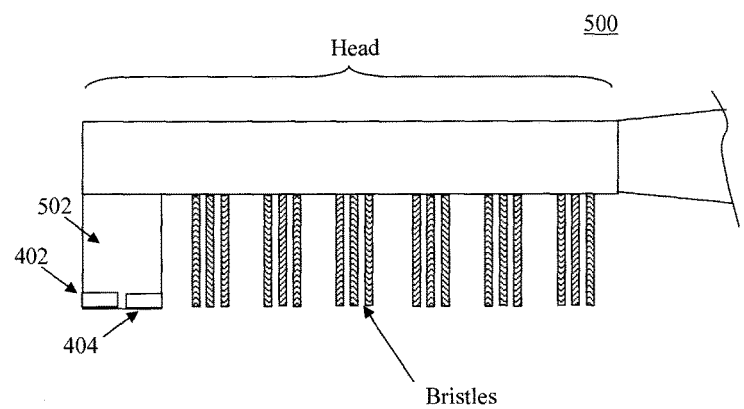
FIG. 5 is a diagram illustrating another exemplary smart toothbrush design having optical sensors according to an embodiment of the present invention.

Another exemplary configuration of the present smart toothbrush platform and use thereof to perform the steps of methodology 100 is now described by way of reference to FIGS. 4 and 5. In this example, optical sensors and detectors in conjunction with a dyed rinse or toothpaste are used to detect bacteria in the mouth. Feedback can then be provided to the user as to when to continue brushing in a certain location(s) to eliminate the bacteria detected.

Referring to FIG. 4, as above, the smart toothbrush platform 400 in this exemplary embodiment has a head portion and a handle portion. In addition to the advances presented herein, the head portion also performs the brushing tasks commonly associated with a toothbrush. For instance, as shown in FIG. 4, the head portion of the toothbrush contains a plurality of bristles (and/or other structures) configured to remove plaque, bacteria, particulates, etc.) from a user's teeth. The handle portion is gripped by the user and used to position and move the head portion/bristles over the teeth.

In the exemplary embodiment shown in FIG. 4, in addition to the bristles, the head portion of the smart toothbrush 400 includes a light source 402 and an optical detector 404. The light source and detector collectively operate as an optical sensor. For instance, according to an exemplary embodiment, the light source is a light emitting diode (LED) and the optical detector is a camera or spectrometer. During brushing, the LED light source will illuminate the tooth surfaces, and images of those illuminated surfaces are captured by the camera. By action of the dyed mouth rinse or toothpaste, areas of bacteria or other germs in the mouth appear a different color which can be picked up by the camera. Dyed mouth rinses and toothpastes are commercially available. As highlighted above, these products bind a dye to germs in the mouth in order to visually aid in the tooth cleaning process.

The handle portion of the smart toothbrush 400 can include a readout display 406. As provided above, feedback can be provided to the user through such a display. For instance, data/data analyses, alerts, instructions, etc. may be displayed to the user. In addition to the readout display, the battery (and/or other power source) and peripheral electronics can also be housed in the handle.

FIG. 5 provides an alternative design for incorporating the optical sensors into the present smart toothbrush head portion 500. For instance, as shown in FIG. 5, instead of being located in between the bristles, the light source 402 and optical detector 404 can instead be embedded in a section of the toothbrush, adjacent to the bristles, that is composed of a deformable foam 502. This will put the light source 402 and optical detector 404 in intimate contact with the tooth surface during brushing since the deformable foam will contour to the tooth surfaces it passes over. An example of deformable foam is, but is not limited to, a dental foam sponge. In this example, the deformable foam platform for the light source 402 and optical detector 404 is placed at the end of the toothbrush head opposite the handle. It is however possible to place these structures at any location amongst the bristles on the toothbrush head.

Figure 6:
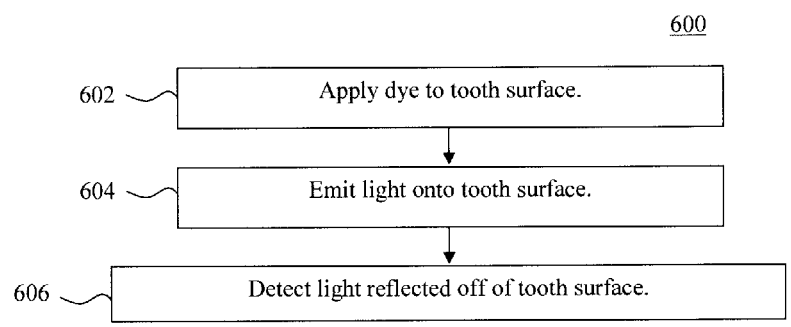
FIG. 6 is a diagram illustrating an exemplary methodology for acquiring user data via the smart toothbrush designs of FIGS. 4 and 5 according to an embodiment of the present invention.

FIG. 6 is a diagram illustrating an exemplary methodology 600 for using smart toothbrush 400 (or the optional toothbrush head design 500) to collect data from a user during brushing. For instance, methodology 600 represents an exemplary process for operating the present smart toothbrush when performing, for example, step 102 of FIG. 1.

As provided above, when optical sensors are employed, the present techniques are used in conjunction with a dyed mouth rinse and/or dyed tooth paste to enable marking certain regions of the mouth during brushing, such as those regions having germ build-up. Thus in step 602, an oral dye is applied to the tooth surface. The dye, contained in the mouth rinse and/or tooth paste, is specific for binding to germs in the mouth. When a dyed mouth rinse is used, the user might gargle with the rinse immediately prior to brushing. A dyed tooth paste can be used during brushing.

Normal brushing activity is then carried out using the present smart toothbrush during which time, in step 604 light generated by the light source 402 is emitted onto the dyed tooth surface. As provided above, a suitable light source is a light-emitting diode (LED). According to an exemplary embodiment, the mouth rinse and/or toothpaste dyes portions of the tooth surface having germs (such as bacteria) a color distinguishable from normal tooth color, such as blue, green, etc.

In step 606, light (from the light source 402) which is reflected from the dyed/undyed portions of the tooth surface is captured by the optical detector 404. The (optical) data acquired by the optical detector 404 can then be analyzed as described in conjunction with the description of step 104 of methodology 100, above, and feedback can be provided to the user, etc. As highlighted above, in this example useful feedback garnered from the analyzed data might include indicating to the user where additional brushing is needed (i.e., due to the detection of dyed areas of the tooth surface indicating germ buildup).

It is notable that the functional aspects of electronic sensors (FIGS. 2 and 3) and optical sensors (FIGS. 4-6) can be incorporated into the same smart toothbrush platform. For instance, embodiments are anticipated herein where both electronic and optical sensors are present on the same toothbrush platform. In that case, the steps of methodologies 300 and 600 can be performed using the same toothbrush design.

Figure 7:
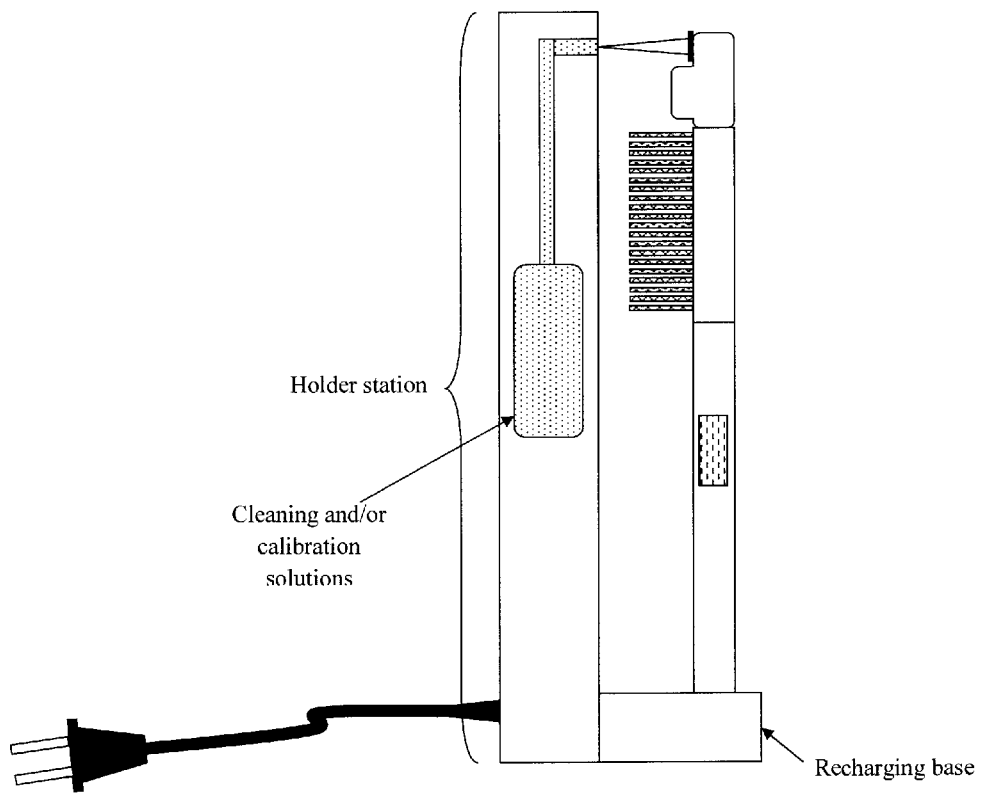
FIG. 7 is a diagram illustrating an exemplary holder station for the smart toothbrush according to an embodiment of the present invention.

As provided above, a holder station may be employed to support the smart toothbrush when not in use, and may also provide some added functionalities such as recharging, cleaning, exchanging data, and/or calibrating the smart toothbrush. An exemplary configuration of the holder station is shown illustrated in FIG. 7. As shown in FIG. 7, the holder station includes a recharging base configured to recharge the battery in the smart toothbrush handle. The recharging base can be connectable to a household power source (as shown) or to an alternative power source (e.g., solar power source, etc.). In this example, the holder station also includes one or more reservoirs containing a cleaning solution(s) and/or calibration solution(s) for the sensors. For instance, as described in detail above, the holder station can contain fluids of known concentrations of desired measurement or reference materials and therefore provide calibration to one or more sensors in the electronic toothbrush.

As provided above, BTJ-based sensors may be used in the electronic sensor design. Advantageously, different sensing surfaces may be employed in the sensors to detect different parameters in the user samples. For instance, BTJ-based sensors employing a TiN sensing surface are pH sensitive (see, for example, Zafar). Alternatively, a silver (Ag) sensing surface can be used in the detection of chloride (Cl) ions. See, for example, Trnkova et al., "Amphoteric Sensor for Detection of Chloride Ions," Sensors, 8, 5619-5636 (September 2008), the contents of which are incorporated by reference as if fully set forth herein. Chloride ions can be used as indicators of renal failure (i.e., hyperchloremia). A gold (Au)-sensing surface can be functionalized with a layer of bio-molecules, such as probe deoxyribonucleic acid (DNA), anti-bodies, enzymes, proteins, etc. See, for example, Das et al., "Mechanistic Influence of Nanometer Length-Scale Surface Chemistry on DNA Hybridization," ACS Nano, 9(7), pgs. 7466-7478 (June 2015), the contents of which are incorporated by reference as if fully set forth herein. The basic detection principle using a BTJ-based sensor is as follows. When charged ions or biomolecules get bound to the sensing surface, this causes the surface potential of the sensing surface to change which in turn cause the sensing current (collector current) to change. Since ions, proteins, DNA, etc. have charges, they all can be detected provided they specifically bind to the sensing surface. Thus, ff the TiN, Au, etc. surface is coated with antibodies, then the sensing surface would bind proteins corresponding to the antibodies.

Advantageously, BTJ-based sensors are small enough that multiple sensors can be incorporated in the head portion of the toothbrush, each sensor being configured to sense different things, e.g., different types of electronic sensors and/or optical sensors, etc. According to an exemplary embodiment, at least one of the following electronic saliva sensors are included in the present smart toothbrush design: cortisol and alpha amylase sensing for anxiety, stress, depression detection, pH, salivary lipase for GI problem and weight control, allergy, cancer, chemistry related to taste and disease.

Figure 8:
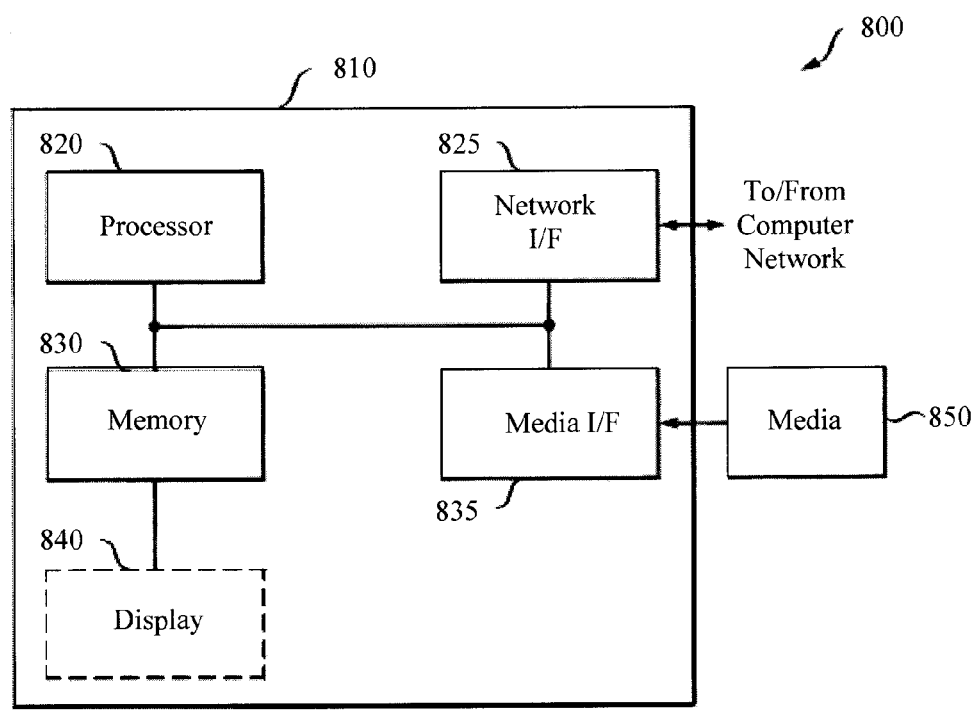
FIG. 8 is a diagram illustrating an exemplary apparatus for performing one or more of the methodologies presented herein according to an embodiment of the present invention.

Turning now to FIG. 8, a block diagram is shown of an apparatus 800 for implementing one or more of the methodologies presented herein. By way of example only, apparatus 800 can be configured to implement one or more of the steps of methodology 100 of FIG. 1 for analyzing data collected by the present smart toothbrush and/or for providing feedback to the user based on the data analysis.

Apparatus 800 includes a computer system 810 and removable media 850. Computer system 810 includes a processor device 820, a network interface 825, a memory 830, a media interface 835 and an optional display 840. Network interface 825 allows computer system 810 to connect to a network, while media interface 835 allows computer system 810 to interact with media, such as a hard drive or removable media 850.

Processor device 820 can be configured to implement the methods, steps, and functions disclosed herein. The memory 830 could be distributed or local and the processor device 820 could be distributed or singular. The memory 830 could be implemented as an electrical, magnetic or optical memory, or any combination of these or other types of storage devices. Moreover, the term "memory" should be construed broadly enough to encompass any information able to be read from, or written to, an address in the addressable space accessed by processor device 820. With this definition, information on a network, accessible through network interface 825, is still within memory 830 because the processor device 820 can retrieve the information from the network. It should be noted that each distributed processor that makes up processor device 820 generally contains its own addressable memory space. It should also be noted that some or all of computer system 810 can be incorporated into an application-specific or general-use integrated circuit.

Optional display 840 is any type of display suitable for interacting with a human user of apparatus 800. Generally, display 840 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A toothbrush, comprising:
a handle portion; and
a head portion attached to the handle portion, wherein the head portion comprises bristles, a sample testing chamber containing at least one electronic sensor, a removable tip for drawing saliva samples into the sample testing chamber, and a calibration solution reservoir connected to the sample testing chamber, wherein the head portion further comprises at least one optical sensor, and wherein the optical sensor is mounted on a deformable foam platform on the head portion.

2. The toothbrush of claim 1, wherein the head portion further comprises a shutter for regulating fluid flow into and out of the sample testing chamber via the removable tip.

3. The toothbrush of claim 1, wherein the head portion further comprises:
a pump system for drawing i) the saliva samples via the removable tip and ii) a calibration solution from the calibration solution reservoir into the sample testing chamber.

4. The toothbrush of claim 1, wherein the calibration solution comprises a known amount of sodium chloride at a controlled pH.

5. The toothbrush of claim 1, wherein the removable tip comprises a filter.

6. The toothbrush of claim 1, wherein the electronic sensor comprises a bipolar junction transistor (BTJ)-based sensor.

7. The toothbrush of claim 6, wherein the electronic sensor comprises:
a heterojunction bipolar transistor (HBT); and
an extended base.

8. The toothbrush of claim 7, wherein the extended base comprises:
a sensing surface; and
a reference electrode.

9. The toothbrush of claim 8, wherein the sensing surface comprises at least one of titanium nitride (TiN) for pH sensing, silver (Ag) for chloride ion sensing, gold (Au) coated with a layer of bio-molecules.

10. The toothbrush of claim 1, wherein the handle portion comprises a readout display.

11. The toothbrush of claim 1, wherein the optical sensor comprises:
a light source; and
an optical detector.

12. The toothbrush of claim 11, wherein the light source comprises a light emitting diode (LED).

13. The toothbrush of claim 11, wherein the optical detector is a camera or a spectrometer.

14. A toothbrush, comprising:
a handle portion; and
a head portion attached to the handle portion, wherein the head portion comprises bristles, and at least one optical sensor, wherein the head portion further comprises a sample testing chamber containing at least one electronic sensor, a removable tip for drawing saliva samples into the sample testing chamber, and a calibration solution reservoir connected to the sample testing chamber, and
wherein the sample testing chamber is located in the head portion in front of the bristles with the removable tip extending out from the sample testing chamber parallel to the bristles, and wherein the removable tip is fitted with a filter.

15. A method for acquiring user data, the method comprising the steps of:
collecting data from a user during toothbrushing using a toothbrush comprising a handle portion and a head portion attached to the handle portion, wherein the head portion comprises bristles, a sample testing chamber containing at least one electronic sensor, a removable tip for drawing saliva samples into the sample testing chamber, and a calibration solution reservoir connected to the sample testing chamber;
analyzing the data using a processor device connected to a memory; and
providing feedback based on the analyzed data to the user via a display on the handle portion which provides visual indicators to the user while toothbrushing,
wherein the head portion of the toothbrush further comprises at least one optical sensor, the optical sensor comprising a light source and an optical detector, the method further comprising the steps of:
applying a dye to a tooth surface of the user;
emitting light onto the tooth surface using the light source; and
detecting the light reflected off of the tooth surface using the optical detector to reveal portions of the tooth surface containing the dye.

16. The method of claim 15, wherein the collecting step comprises the steps of:
drawing a calibration solution from the solution reservoir into the sample testing chamber;
taking readings of calibration solution using the electronic sensor;
ejecting the calibration solution from the sample testing chamber;
drawing a saliva sample into the sample testing chamber via the removable tip;
taking readings of the saliva sample using the electronic sensor;
ejecting the saliva sample from the sample testing chamber; and
drawing fresh calibration from the solution reservoir into the sample testing chamber.

* * * * *